United States Patent [19]

Jannard

[11] Patent Number: 4,859,048

[45] Date of Patent: * Aug. 22, 1989

[54] CYLINDRICAL LENS FOR SUNGLASSES

[75] Inventor: James H. Jannard, Laguna Niguel, Calif.

[73] Assignee: Oakley, Inc., Irvine, Calif.

[*] Notice: The portion of the term of this patent subsequent to Jun. 23, 2004 has been disclaimed.

[21] Appl. No.: 65,345

[22] Filed: Jun. 23, 1987

Related U.S. Application Data

[63] Continuation-in-part of Ser. No. 690,642, Jan. 11, 1985, Pat. No. 4,674,851, and Ser. No. 893,091, Aug. 4, 1986, abandoned.

[51] Int. Cl.$^4$ ............................................. G02C 7/02
[52] U.S. Cl. ...................................... 351/159; 351/44; 351/47
[58] Field of Search .................... 351/44, 47, 62, 103, 351/109, 158, 159; 2/426, 429

[56] References Cited

U.S. PATENT DOCUMENTS

| | | |
|---|---|---|
| 145,288 | 7/1946 | Di Cicco . |
| 163,869 | 7/1951 | Hinman . |
| 176,316 | 12/1955 | Fleming . |
| 178,178 | 7/1956 | Fleming . |
| 187,394 | 3/1960 | Moeller . |
| 199,150 | 9/1964 | Carmichael . |
| 210,048 | 1/1968 | Imperatrice . |
| 268,683 | 4/1983 | Tenny . |
| 285,020 | 9/1986 | Schmidthaler . |
| 2,444,498 | 7/1948 | Cochran . |
| 2,472,731 | 6/1949 | Splaine . |
| 2,482,664 | 9/1949 | Gagnon . |
| 2,582,345 | 1/1952 | Moeller . |
| 3,133,982 | 5/1964 | Janz . |
| 3,233,249 | 2/1966 | Baratelli et al. . |
| 3,233,250 | 2/1966 | Jonassen . |
| 3,531,189 | 9/1970 | Petito . |
| 3,689,136 | 9/1972 | Atamian . |
| 3,708,224 | 1/1973 | Linblom . |
| 3,756,704 | 9/1973 | Marks . |
| 4,515,448 | 5/1985 | Tackles . |
| 4,564,272 | 1/1986 | Kan . |
| 4,674,851 | 6/1987 | Jannard ............................. 351/47 |
| 4,730,915 | 3/1988 | Jannard ............................. 351/44 |

FOREIGN PATENT DOCUMENTS

| | | |
|---|---|---|
| 673815 | 1/1930 | France . |
| 790755 | 11/1935 | France . |
| 2472764 | 7/1981 | France . |

OTHER PUBLICATIONS

Picture of Oakley Blades as first worn 8/27/85.

Primary Examiner—Rodney B. Bovernick
Assistant Examiner—P. M. Dzierzynski
Attorney, Agent, or Firm—Knobbe, Martens, Olson & Bear

[57] ABSTRACT

Disclosed is a cylindrical lens for use in a pair of sunglasses, comprising a unitary pane of transparent material curved about an axis and having a substantially constant radius such that the lens defines a portion of the wall of a cylinder. The arc length measured from a first distal end along the lens to a second distal end is within the range of about 5½ to about 7 inches so that the lens covers both eyes of the wearer and effectively shields the eyes from peripheral as well as direct bright light. The lens may have either a uniform thickness throughout, or may taper from a greater thickness in a region centered about the midpoint, generally above the nose of a wearer, to a lesser thickness near the peripheral ends of the lens.

16 Claims, 5 Drawing Sheets

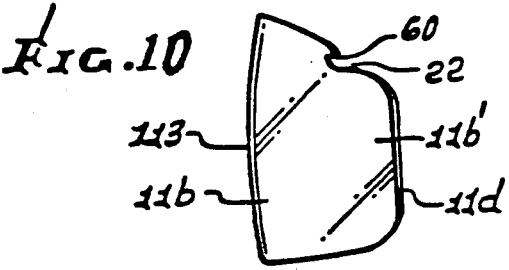
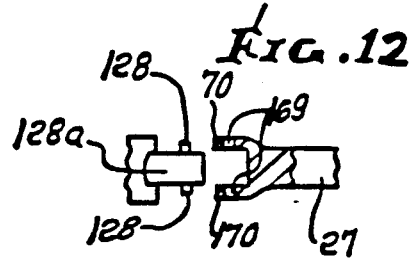
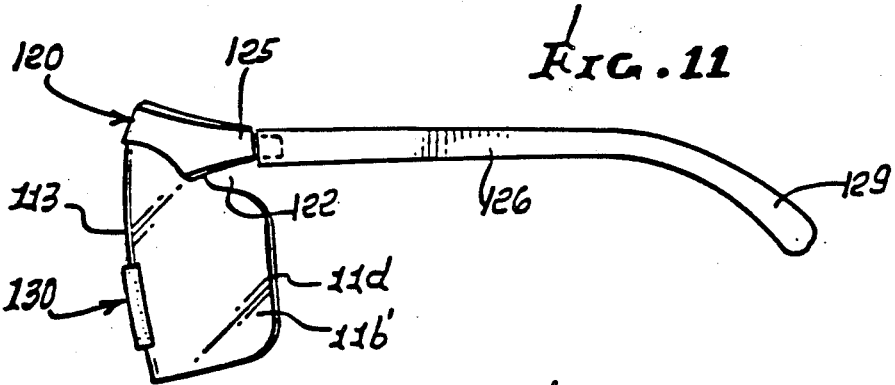
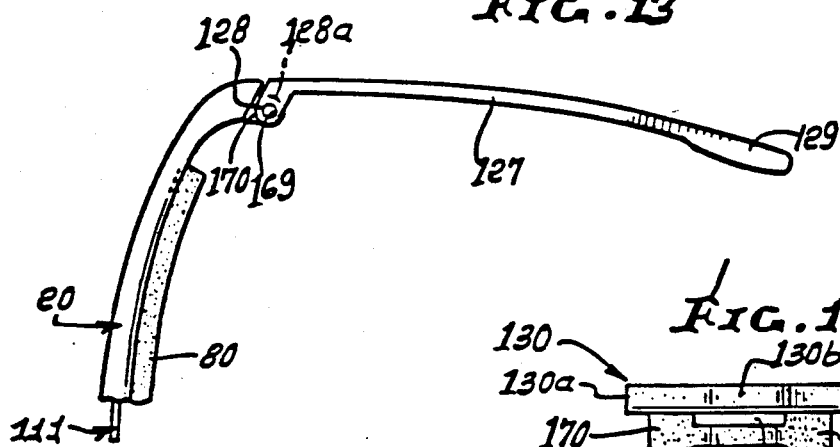
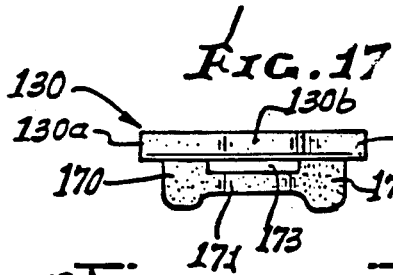
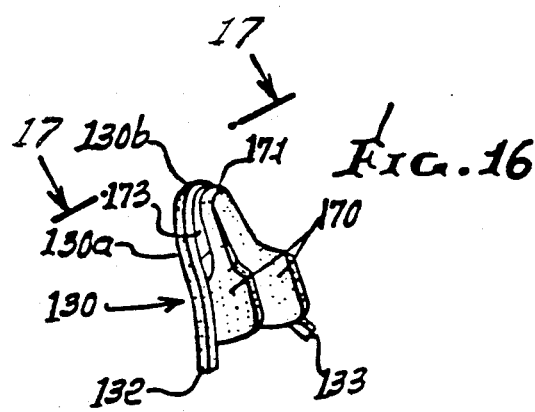
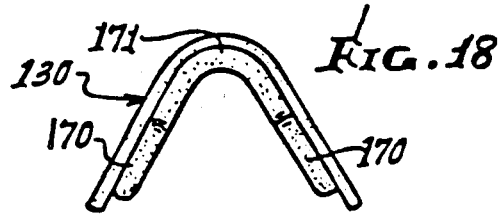

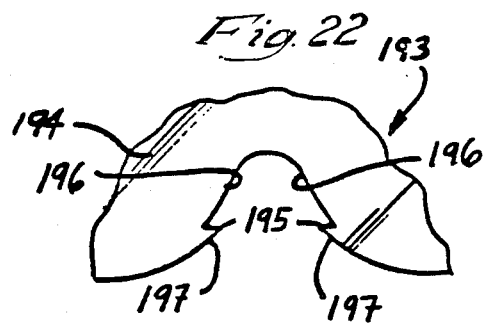
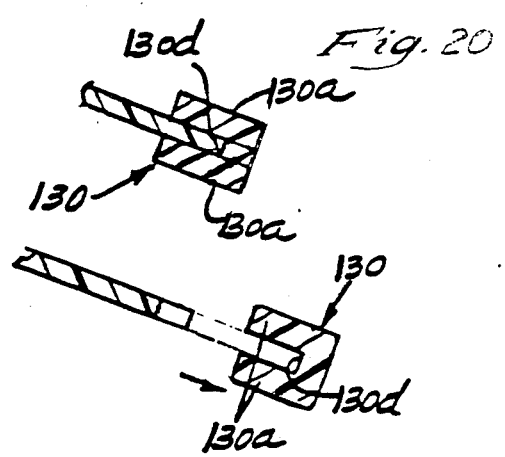
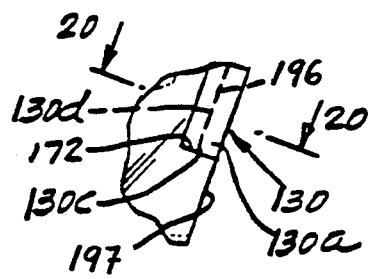

CYLINDRICAL LENS FOR SUNGLASSES

BACKGROUND OF THE INVENTION

This application is a continuation in part of Ser. No. 690,642, now U.S. Pat. No. 4,674,851 filed Jan. 11, 1985, and of Ser. No. 893,091, now abandoned filed Aug. 4, 1986.

The present invention relates to a lens for sunglasses, and, more particularly, to a unitary, high quality, substantially cylindrical lens having exceptional optical clarity, and which extends substantially unobstructed throughout the wearer's entire angular range of vision. The lens of the present invention maximizes the interception of peripheral light, while, at the same time, permits sufficient ventilation to remain comfortable and resist fogging. The cylindrical configuration of the lens also permits construction of sunglasses which conform closely to the front and sides of the wearer's head. The resulting low profile glasses utilizing the lens of the present invention are particularly suited for demanding situations which require precise optical resolution and interception of peripheral light, such as competition skiing or bicycle racing.

Sunglasses have long been designed with the general objective of blocking the sun or other sources of bright light from one's eyes. Numerous designs of dual lens glasses have been developed, differing essentially only in aesthetic features. Although useful for some purposes, the dual lens system is inherently incapable of meeting the demands of certain activities. For example, the frame on dual lens glasses presents a substantial obstruction to one's peripheral vision, which can be extremely disadvantageous in any fast-paced activity. Even in dual lens glasses without a frame along the lower edges of the lenses, the edge of each lens disrupts peripheral vision. Simply providing a larger lens, which is typically stamped or molded from a flat plane or a spherical blank, causes the glasses to extend too far tangentially away from the side of the head, leaving the glasses with an undesirably bulky profile.

At the same time, the dual lens glasses only intercept sunlight directly in front of the eye, leaving a large, unprotected periphery about each lens. Momentary flashes of light around the lens during activity causes constriction of the pupils, with a fleeting blindness as one attempts to readjust through the darkened lens.

Prior art attempts to block peripheral light (aside from opaque blinders) included bending a flexible lens in an anterior direction near the lateral edge. Although this improved the interception of peripheral light, the resulting optical resolution was unacceptable for high speed competition situations. This is due to the phenomena that even minor irregularities in the radius of curvature, which inherently result when bending a lens, cause an irregular diffraction of lightwaves passing through that region of the lens and distort the field of vision.

The unitary, molded, frusto-conical lens blank was then developed, such as that disclosed in U.S. Pat. No. 4,515,448 to Tackles. Although diffraction gradients were minimized by molding the lens with a predetermined curvature, the unitary frusto-conical lens remained unsatisfactory for several reasons.

One principal dissatisfaction with the frusto-conical lens is that the lens tends to conform so closely to the wearer's head that adequate ventilation is not possible. Indeed, reference to Alderson's head forms, which are generally accepted standards for typical anatomical structure, reveal that the front of the human head very closely conforms to a frusto-conical plane. As a result, the lens very closely conforms to the forehead at the top and to the cheek bones at the bottom thereof. If the dimensions of the glasses are reduced to leave a gap for ventilation, they no longer sufficiently intercept light. Alternatively, if the lens is curved outwardly, for example, away from the cheek bone, the optical quality of the lens is impaired.

An additional disadvantage of the frusto-conical lens from a manufacturing standpoint, is that the mold for producing a lens blank of that shape is very difficult to polish. In the manufacturing process, molded unitary curved lens blanks cannot be buffed or polished. Instead, they must come out of the mold perfectly clear. This requires periodic polishing of the hardened steel mold to a uniform, mirror-smooth surface which, for mechanical reasons, is difficult to economically accomplish for a frusto-conically shaped mold. As a result of very minor rough areas and depressions which develop on the mold surface, a slight fogging of the lens occurs, as well as variations in thickness, rendering it unsuitable for many specialized activities.

Thus, notwithstanding the numerous attempts in the prior art, Applicant is unaware of any sunglasses which have both excellent optical properties and interception of peripheral light, yet at the same time have a sleek, low profile, and adequate ventilation, such as the glasses disclosed herein.

SUMMARY OF THE INVENTION

There has been provided, in accordance with one aspect of the present invention, a unitary curved lens for mounting any frame to form a pair of eyeglasses, conformed to extend in the path of the wearer's left and right eye fields of vision. The lens comprises a unitary pane curved about an axis and having a substantially constant radius throughout, such that the lens defines a portion of the wall of a cylinder. This configuration eliminates the need for multiple frame support mechanisms and enhances the unobstructed field of the wearer's vision. In addition, the curvature of the present lens permits it to conform closely from side to side to the wearer's face, thus maximizing the interception of sun and other strong light sources, both directly in front and peripherally, while at the same providing comfort and pleasing esthetic characteristics.

The lens has an arc length measured from a first distal end of the lens along the curved arc of the lens to a second distal end of from about $5\frac{1}{2}$ to about 7 inches. The radius of the arc defining the inner concave surface of the cylindrical lens is within the range of from about 2.5 to about 4.5 inches. The height of the lens measured in an axial direction is greater in the area of each of the distal ends than at a point intermediate said ends in order to provide an accommodating opening for the nosepiece. Thus, the lens is divided into two eye panes, each having a height within the range of from about $1\frac{3}{4}$ to about 3 inches. The area intermediate the two eye panes which is of reduced height in order to accommodate the nosepiece typically has a height dimension of within the range of about $\frac{3}{4}$ inch to $1\frac{1}{2}$ inches. The thickness of the lens in the foregoing embodiment is substantially uniform throughout the arc length thereof.

In accordance with another embodiment of the lens of the present invention, the thickness of said lens is less at the first and second distal ends thereof than at a point midway therebetween. Preferably, the thickness of the lens at a point approximately 45° along the arc thereof from the midpoint will be from about 40% to about 99% of the average thickness of the lens in a region near the midpoint thereof. The ratio of the height of the lens in an axial direction through the eye pane to the arc length of the lens is typically within the range from about 0.30 to about 3.50. The ratio of the radius of the arc defining the interior concave surface of the lens to the arc length of the lens is in the range of from about 0.35 to about 0.80.

Further objects, features and advantages of the present invention will become apparent from the Detailed Description of Preferred Embodiments which follows, when considered together with the attached figures and claims.

DESCRIPTION OF THE DRAWINGS

FIG. 10 is a side view of the curved pane, in as-molded condition;

FIG. 11 is a side view of the assembled sunglasses;

FIG. 12 is an inner side view of the ear stem detached from the top frame;

FIG. 13 is a top plan view showing the frame and stem hinge structures, and padding;

FIG. 16 is a perspective view of a nosepiece with attached elastomeric pads to engage the sides of the wearer's nose;

FIG. 17 is top plan view on lines 17—17 of FIG. 16;

FIG. 18 is a front view on lines 18—18 of FIG. 17;

FIG. 19 is an enlarged frontal view showing fit of a nosepiece to the FIG. 22 lens sheet;

FIG. 20 is an enlarged section taken on lines 20—20 of FIG. 19;

FIG. 21 is a view like FIG. 20, but showing inward retraction of a grooved nosepiece from the lens sheet edge, for removal of the nosepiece;

FIG. 22 is a fragmentary view of a modified lens sheet.

DETAILED DESCRIPTION OF THE PREFERRED EMBODIMENTS

Referring to FIGS. 1-4, there has been provided in accordance with one aspect of the present invention a unitary curved lens 12 for mounting in a frame 13 to form a pair of eyeglasses 14, conformed to extend in the path of the wearer's left and right eye fields of vision.

Figure 1:
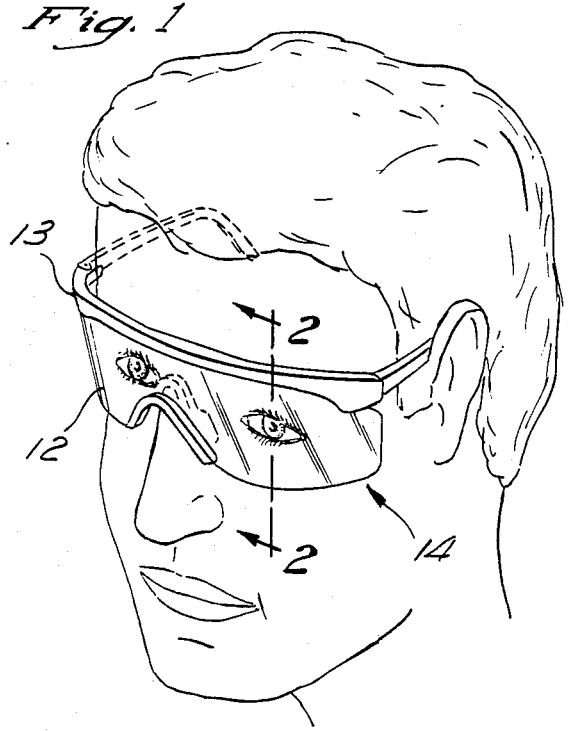
FIG. 1 is a perspective view of a pair of sunglasses including a lens made in accordance with the present invention, on the head of a wearer.

The curvature of the unitary lens 12 of the present invention is substantially cylindrical, thereby eliminating the need for multiple frame support mechanisms and enhancing the unobstructed field of the wearer's vision. As shown in FIG. 1, the curvature of the present lens 12 permits it to conform closely from side to side to the wearer's face, thus maximizing the interception of sun and other strong light sources, while at the same time providing comfort and pleasing esthetic characteristics.

Figure 2:
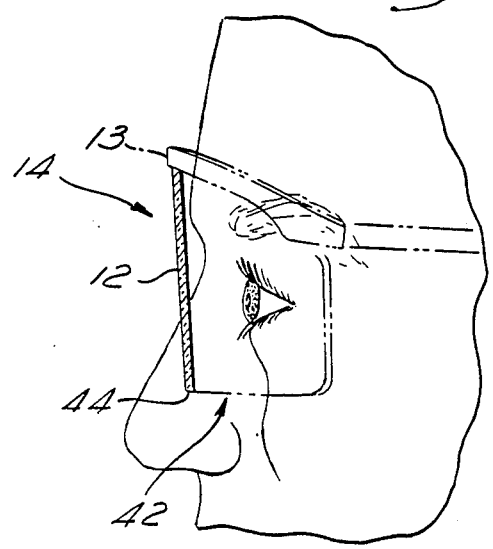
FIG. 2 is a vertical sectional view of the lens of the present invention, on the head of a wearer.

Looking at the lens 12 from top to bottom, as shown in FIG. 2, the lens curvature permits it to conform closely to the face of the wearer along its upper edge, while providing a ventilation space 42 along its lower edge, as explained below in more detail. FIG. 2 also illustrates the upward curvature of the upper edge of the lens which intercepts downwardly incident light rays.

Figure 3:
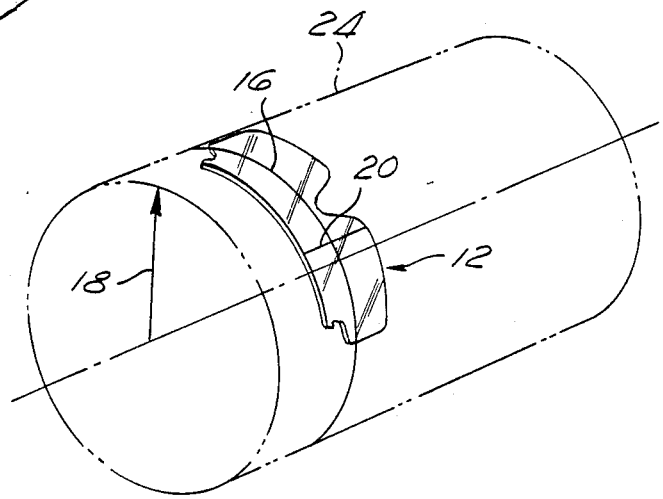
FIG. 3 is a perspective view of the cylindrical lens of the present invention shown conforming to a cylinder.
Figure 4:
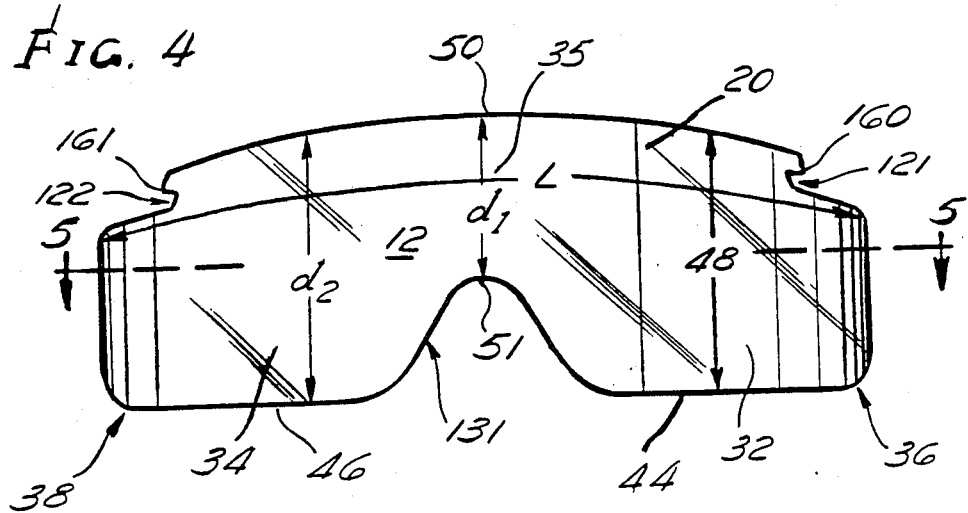
FIG. 4 is an elevational view of the lens of the present invention.

FIG. 3 illustrates the present lens 12 substantially conforming to the exterior surface of a curved geometrical body, such as a cylinder 24. Since the present lens 12 is molded in this configuration, it does not have to be bent or twisted to conform to the wearer's face or to a mechanism for supporting the lens on the face, thus avoiding optical distortion due to such bending or twisting.

Thus, the lens of the present invention is preferably provided with a substantially uniform curve, such that a line 16 (FIG. 3) drawn along the surface of the lens 12 in a circumferential direction defines an arc of substantially uniform radius 18, as shown in FIG. 3. At the same time, a line 20 drawn along the surface of the lens 12 in an axial direction is substantially parallel to the axis of a cylinder 24 (illustrated in FIG. 3). Thus, the lens of the present invention is provided with a curve such that it substantially conforms to a portion on the surface of a cylinder.

Optimally, the lens 12 has a radius of curvature 18 in the "as-molded" condition which is substantially unchanged by mounting the lens 12 in a pair of eyeglass frames 13. It has been determined that optical properties of a lens are detrimentally affected by deviations from the as-molded condition. For example, bending a lens cut from flat sheet stock or a flat molded blank to provide a cylindrical curvature inherently results in minor variations in the radius along the arc length of the lens. Variations in the light diffraction properties of the lens result, which introduce distortion. In addition, bending a lens can also result in stress fractures or other compression or expansion induced flaws which can impair the optical qualities of the lens.

Thus, the lens is preferably pre-molded to the desired configuration. Although a variety of radii might accrue the advantages of the present invention, the lens is preferably molded to a radius 18 within the range of from about 2.50 to about 4.50 inches, and preferably within the range of from about 3.50 to about 4.00 inches. The foregoing radius dimensions represent the distance from the axis to the arc which defines the interior, concave portion of the lens. The lens of the present invention has sufficient thickness that it is not accurately defined as having only a single radius. Instead, referring to FIG. 5, the lens 12 has a thickness or depth dimension 26 along its entire arc length which causes the arc defined by the outer, convex surface 28 to have a different radius $R_1$ than the radius $R_2$ of the arc defined by the inner, concave surface 30 of the lens 12. Hence, the radius $R_1$ of the convex surface 28 is essentially equal to the sum of the radius $R_2$ of the concave surface 30 and the depth 26 of the lens in the foregoing embodiment.

The foregoing discussion pertains to the contour of the lens, as distinguished from its shape, which will now be discussed. The shape of one embodiment of the lens may be best understood by reference to FIG. 4, although many other shapes can be envisioned which will accrue the advantages of the present invention.

A first eye pane 32 and a second eye pane 34 are located directly in front of the wearer's left and right eyes, respectively, and are merged together with a unitary bridge portion 35. In addition, the distal portion 36 of eye pane 32, for example, continues along the arc path of the lens 12, as discussed above in connection with FIG. 3, such that it preferably traverses the entire angular range of vision for the corresponding eye. Similarly, the distal portion 38 of eye pane 34 extends substantially all the way across the wearer's angular range of vision for the other eye. In this manner, a substantial amount of light which approaches the eye from a peripheral direction will travel through the lens before reaching the wearer's eyes.

The objective of shielding against peripheral light is best accomplished in a lens having a radius within the above-stated ranges, if the arc length of the lens is within the range of from about $5\frac{1}{2}$ to about 7 inches. The arc length of the lens is the length along the surface of the lens from a first distal end 58 to a second distal end 59, illustrated in FIG. 6.

Another aspect of the lens of the present invention is that not only does it effectively block peripheral light, but it still permits sufficient ventilation to remain comfortable and to resist fogging. This is accomplished by the linear conformation of the lens along the axial line 20 illustrated in FIG. 3 as well as by the height of the lens. Due to the substantially cylindrical configuration of the lens 12, a frame 13 can be provided for supporting the lens 12 which closely conforms to the shape of the wearer's forehead. This provides a seal against wind, which, for example, in the case of a bicycle rider is directed at a downward angle such as that indicated by the arrow 40 in FIG. 2. In addition, a band of an absorbent material 80 can be disposed between the frame 13 and the forehead to prevent perspiration from entering the wearer's eyes. See, for example, FIG. 13.

At the same time, the axial line 20 of the cylindrical lens 12 gradually increases in distance from top to bottom away from the receding profile of the wearer's face, which is roughly defined by a frusto-conical curve. Thus, as can be seen in FIG. 2, a ventilation gap 42 results between the lower edges 44 and 46 of eye panes 32 and 34, respectively, and the wear's face. This is a significant advantage over the prior art frusto-conical lens. For a lens dimensioned as described herein, ventilation gap 42 will be roughly from about 3/16 to about 5/16 inch greater than the corresponding gap, if any, in the frusto-conical system.

The size of the ventilation gap 42 will also depend in part upon the height 48 of the lens, illustrated on eye pane 32 (FIG. 4) for convenience. It is understood that the height of the eye panes 32 and 34 will be essentially the same and the discussion in connection with one is intended to apply to both.

The height 48 ($d_2$) of the lens 12 of the present invention, measured from the top 50 of the lens 12 to the bottom edge 44, may be varied to optimize various functional and aesthetic considerations, but will typically fall within the range of from about $1\frac{3}{4}$ to about 3 inches, and, preferably between about 2 and $2\frac{3}{4}$ inches. As previously discussed, the two eye panes 32 and 34 merge into a unitary lens by way of a connecting bridge portion 35. The distance ($d_1$) from the top 50 of the lens to the lower edge 51 of the bridge portion 35 may also vary, but preferably is within the range of from about $\frac{3}{4}$ inch to about $1\frac{1}{2}$ inches.

Figure 6:
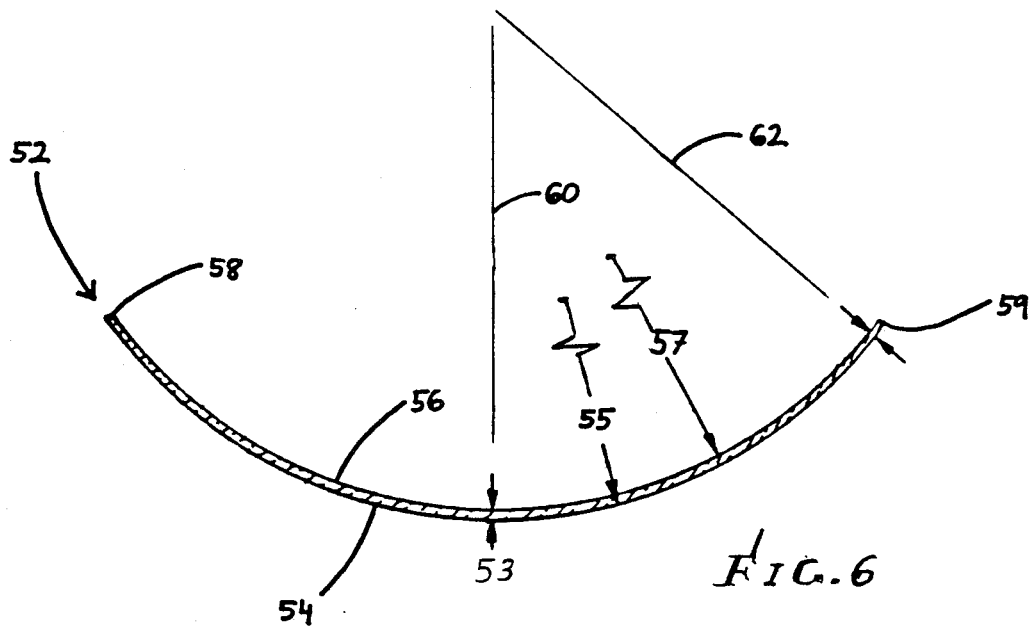
FIG. 6 is a horizontal sectional view like that in FIG. 5, of a second embodiment of the lens of the present invention.

In accordance with another embodiment of the cylindrical lens of the present invention, there has been provided a unitary lens substantially as described above, with the following modification. Referring to the horizontal sectional view of the present embodiment, as illustrated in FIG. 6, there is disclosed a lens 52 defined between an outer convex surface 54, having a radius 55, and an inner concave surface 56, having a radius 57. The principal difference from the previously detailed embodiment is that the thickness of the lens 52 at each of the distal ends 58 and 59 is less than or equal to the average thickness of the lens at every point 53 intermediate the two distal ends 58 and 59. In addition, the thickness of lens 52 measured at least one point intermediate the two ends 58 and 59 is greater than the thickness at each of those ends.

The invention can best be understood by reference to FIG. 6, which illustrates the relationship between the lens thickness and angular position along the arc length of a lens. Since the arc length of a lens can be varied considerably, although it is preferably within the range of from about $5\frac{1}{2}$ to 7 inches, reference points will arbitrarily be selected at the centerline 60 and at the 45° line 62. Thus, since the distance from centerline 60 to reference 62 is $\frac{1}{8}$ of 360°, the reference arc length for a radius of 3 inches is about 4.7 inches which is well below the preferred range.

In accordance with the tapered lens embodiment of the present invention, the thickness of the lens at reference line 62 is preferably from about 40% to about 99% of the thickness at centerline 60. Thus, for example, a lens having a centerline thickness of about 0.060 inches will preferably have a thickness of within the range of about 0.024 to about 0.059 inches at reference line 62, and a thickness near the distal end within the range of about 0.040 to about 0.055 inch. The thickness of the lens at the midpoint is preferably within the range of from about 0.055 to about 0.070 inch.

Preferably, the thickness of the lens tapers at a substantially even rate from the widest region which is centered about centerline 60, to narrower regions near each of the distal ends 58 and 59. In this manner, optical distortion is minimized, as has previously been discussed.

By even rate it is meant that the taper results from the convergence of an arc defining the outer surface 54 of lens 52, and an arc defining the inner surface 56 of lens 52, each arc characterized by constant radii 55 and 57, respectively. Although the surfaces need not be perfectly uniform arcs, as in the previously discussed embodiment, conformation of the lens surface to a substantially constant radius curve accrues important optical advantages. The foregoing may be accomplished in a variety of ways, such as for example, by making radius 55 equal to radius 57 and displacing the center points from each other. Alternatively, radius 55 may be greater or lesser than radius 57, so long as the converging geometry results.

In the production lens, of course, the distal ends 58 and 59 are formed well before the continuation of the arcs defining surfaces 54 and 56 converge. In a cylindrical lens produced in accordance with this embodiment, for example, and having a centerline thickness of approximately 0.060 inches, the thickness at a point proximate either distal end 58 or 59 will generally be within the range of from about 0.040 to about 0.055 inch.

Finally, since a portion of the lens 52 near the distal ends 58 and 59 serves primarily to block peripheral light and is likely outside of the wearer's line of vision, it is less crucial that the radius of curvature be constant in this area. Thus, the lens may be provided with a smooth taper only up to a certain point intermediate the reference line 62 in FIG. 6 and the distal end 59. From that point until the distal end 59, the lens 52 may be provided with a relatively constant thickness or a taper of a different rate. Perhaps less desirable from a manufacturing standpoint, this embodiment could still accrue the advantages of the present invention.

Figure 5:
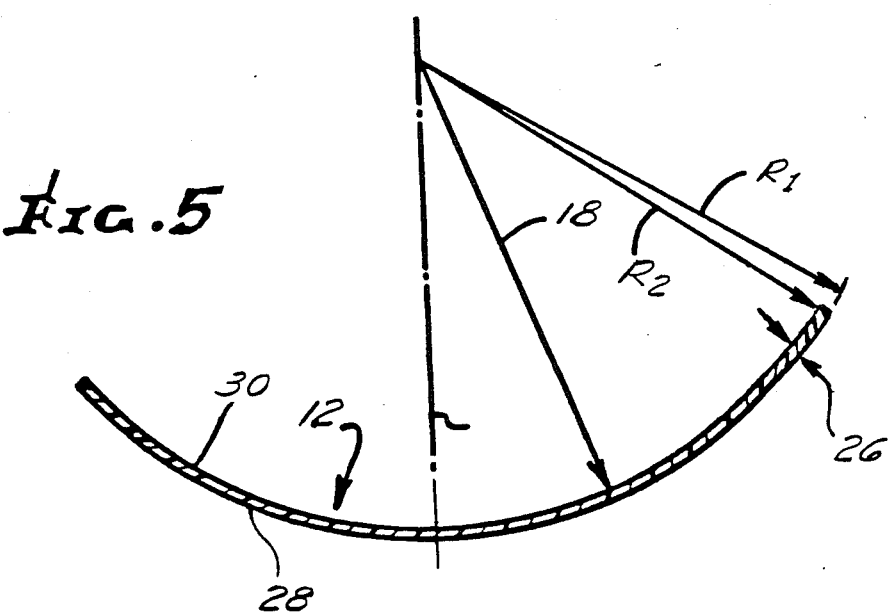
FIG. 5 is a horizontal sectional view taken along the line 5—5 in FIG. 4, showing a first embodiment of the lens of the present invention.
Figure 7:
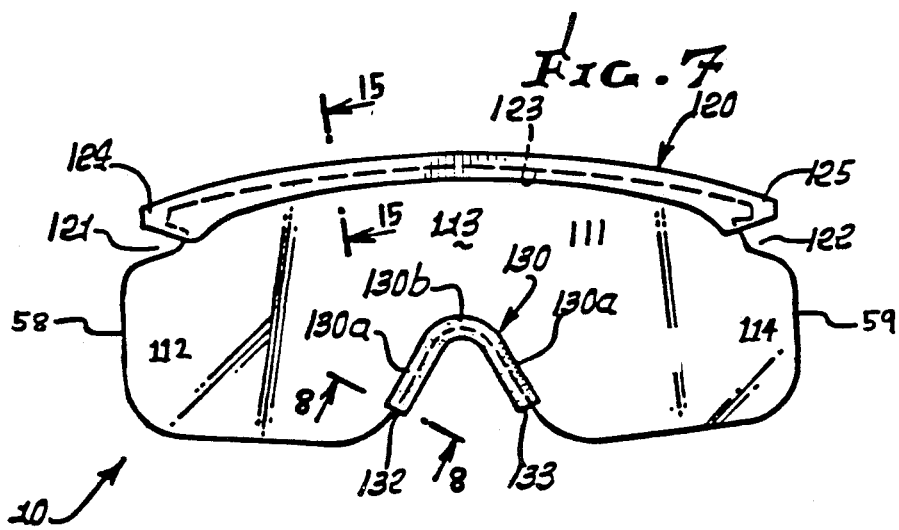
FIG. 7 is an elevational view of the lens of the present invention mounted on an eyeglass frame.

Referring to FIG. 7, the lens of the present invention may be provided with a top frame 120 extending along and bounding the upper edge 50 of the lens or pane 111, which may be either the substantially constant thickness lens illustrated in FIG. 5, or the tapered thickness lens illustrated in FIG. 6. Frame 120 preferably bounds the upper edge 50 of lens 111 along the area between the notched areas 121 and 122 formed immediately above the individual eye panes 112 and 114. The frame advantageously consists of relatively rigid, molded plastic material, which may be transparent or dyed any of a variety of colors.

Figure 15:
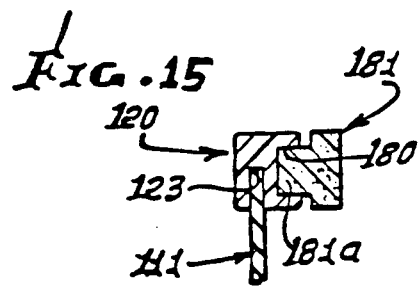
FIG. 15 is an enlarged section taken on lines 15—15 of FIG. 7, to show frame slots for both the pane and padding.

The top frame 120 is shown as being removably attached to the top edge 50 of the lens 111. For this purpose, a slot 123 is formed upwardly therein (FIG. 15) from the bottom of the frame 120, with curvature generally matching that of the lens, to tightly, yet removably receive the lens upper edge 50. The curvature of the slot 123 may be slightly different than the cylindrical, as-molded curvature of the lens, to provide a mismatch, to grip the pane, which then resiliently co-acts with the frame to very slightly deform the pane to frusto-conical shape. Note that the lens upper edge 50 is shown to have slight upward convexity, in FIG. 4, as well as cylindrical curvature, as in FIG. 5. Fastening means such as one or more tangs 160, 161 (see FIG. 4) integral with the pane 12 and projecting over notched areas 121 and 122 fit in corresponding shallow recesses 162 in the frame, at opposite ends of the slot 123, to help retain the pane in position. See FIG. 7.

The top frame has enlarged end terminals at 124 and 125, portions of which extend in notched areas 121 and 122. In addition, terminals 124 and 125 are movably attached to two stems or arms 126 and 127 adapted to extend rearwardly to the wearer's ears (FIGS. 11 and 13). Attachment may be, for example, by trunnions 128 or tongue 128(a) integral with top frame 120, and the bearings or openings 169 in flanges 170 integral with the stem, illustrated in FIGS. 12 and 13. These elements may be of molded, resilient plastic construction and designed to forcibly interfit, and to allow forcible "pullaway," as during impact, for the safety of the wearer. Stems 126 and 127 hook at 129 over the wearer's ears, and may also consist of molded plastic material.

A nosepiece 130 may be provided as illustrated in FIGS. 16–18, which bounds the pane upwardly humped lower edge 131 (see FIG. 4), and has terminals 132 and 133 which are laterally spaced apart to be located along the edge 131 of the pane. The nosepiece has upwardly extending sections 130(a) which taper toward one another, in matching relation to pane edge 131. An upwardly convex section 130(b) interconnects the sections 130(a). The nosepiece has a slot 134 formed therein to extend along the wave-shaped length of the nosepiece for removable interfit with the pane upwardly humped lower edge 131, as seen in FIGS. 8 and 9.

Figure 8:
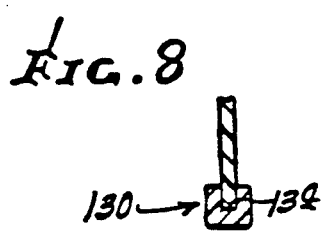
FIG. 8 is an enlarged section through the line 8-8 on FIG. 7, showing a portion of the nosepiece mounting.
Figure 9:
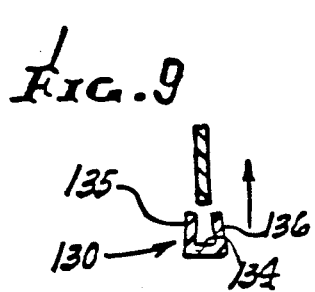
FIG. 9 is an exploded view of the illustration in FIG. 8, prior to assembly of the nosepiece to the pane.
Figure 14:
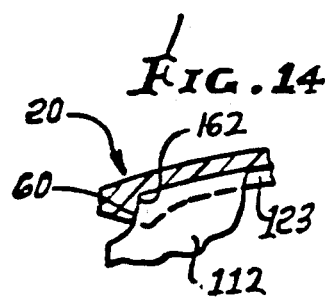
FIG. 14 is an enlarged fragmentary section showing the tang interfit of the unitary pane and top frame.

FIG. 9 shows the nosepiece 130 as channel shaped in cross-section, with flanges 135 and 136 that taper toward one another, to be spread apart upon reception of the pane, as seen in FIG. 8, providing a removable grip or retention of these elements.

The nosepiece 130 preferably comprises a relatively soft elastomeric material having a coefficient of sliding friction that increases when the material is wetted. Such a material is preferably hydrophilic, and tends to retain the nosepiece in position on the wearer's upper nose area as the wearer perspires, or encounters moisture as during skiing. Also, the preferred material is soft, for comfort. One such material is KROTON G, a product of Shell Oil Company.

FIGS. 16–18 show the provision of elastomeric pads 170 connected to the nosepiece 130, and adapted to flex and closely fit the opposite sides of the wearer's nose. A V-shaped elastomeric connector 171 joints the pads to reinforce them and yieldably resist pad flexing. Connector 171 parallels the nosepiece at 130(b), and they define a ventilation slot 173 therebetween to pass air to the rear side of the pane 111 bridge section 113, to resist fogging. See, for example, FIG. 17.

The nosepiece 130 and attached pads 170 may be removed, relatively downwardly, and replaced with a selected substitute, having different size, shape or color, to meet the needs of the wearer. The top frame may also be easily removed upwardly from the pane, and replaced with a different size or color frame. Alternatively, the pane itself may be replaced with a substitute having different sun blocking shading or composition, color, etc. Thus, the wearer or user may assemble his sunglasses from a large number of different components, as provided on a rack or other display, to result in an assembled sunglasses truly best fitted and best suited, component wise, in every respect to the requirements of the wearer.

The notches or notched areas 121 and 122 that extend downwardly proximate the attachments of the hinged connections of the arms to the top frame also open sidewardly. It is found such upper notches draw discharge moisture collecting on the rearward surfaces of the pane, and below the top frame (which projects rearwardly from the top of the pane). Such discharge is believed due to an aspirating affect of air directed laterally toward the notches at the front of the pane, during forward movement of the wearer (as for example a skier). Also, air turbulence at the rearside of the pane is reduced due to presence of the notches. Accordingly, the wearer's eyes are further protected from air turbulence and moisture, and during skiing, wind surfing, etc.

The frame 120 may also be provided with a second slot 180 sunk in its rearward side (see FIG. 15) to receive a tongue portion 181(a) of a foam pad strip 181. Padding 181 is adapted to engage the wearer's forehead, for comfort, whereby the sunglasses are yieldably supported on the wearer's nose by flexing elastomeric pads 170, and by engagement of pad 180 with the wearer's forehead, as during force application to the sunglasses toward the wearer's face.

FIGS. 19–22 show the nose portion 193 of a modified lens sheet 194 which is otherwise constructed as is lens sheet 111. It has an inverted V-shaped lower edge defining upwardly facing shoulders 195 that act to block downward displacement of the lower ends 132 and 133 of the V-shaped lower frame 130, seen in FIG. 16. The lens sheet has two pairs of edges, each shoulder 195 extending between the edges 196 and 197 of each pair. As the nosepiece 130 is pushed upwardly into position, its leg sections 130(a) ultimately snap outwardly away from one another, so that the lowermost end 130(c) of each leg section engages a shoulder 195. Note that each leg section is grooved, as at 130(d), to receive the edge extent of the lens sheet. To remove the nosepiece, the leg sections are press-deflected toward one another so that the lower ends of the leg sections clear the shoulders 195, and the nosepiece is then removed downwardly.

Although this invention has been described in terms of certain preferred embodiments, other embodiments that are apparent to those of ordinary skill in the art are also within the scope of this invention. Accordingly, the scope of this invention is intended to be limited only by the appended claims.

What is claimed is:

1. An arcuately molded lens for eyeglasses, said lens being mounted on the wearer by means of an eyeglass frame having a lens-receiving portion and a pair of ear stems, and suitable for participation in active sports, such as biking, skiing, and the like, said lens comprising:

a unitary lens having an upper edge and a lower edge, said lower edge having a nosepiece opening formed therein for mounting said lens on the nose of the wearer, thereby mounting said lens, in cooperation with said eyeglass frame, on the head of the wearer, said upper edge of said lens having a generally upwardly arcuate configuration to maximize the surface area of said lens above the eye level of said wearer in order to intercept light rays incident from above, said lens having a bright portion over said nosepiece opening, the distance separating the lower edge of the bridge portion and the top of the lens being defined as $d_1$, and the distance separating the bottom edge of the lens and the top of the lens being defined as $d_2$, wherein $d_1$ is in the range between about $\frac{3}{4}$ inch and $\frac{1}{2}$ inches, and $d_2$ is in the range from about $1\frac{3}{4}$ inches to $2\frac{3}{4}$ inches, said dimensions providing optimum interception of light rays while allowing sufficient ventilation around the face of the wearer while participating in active sports, said lens having in its as-molded condition an arcuate cross-sectional configuration wherein the arc length (L) of said lens is in the range of about $5\frac{1}{2}$ to about 7 inches, and wherein the plane of said lens substantially defines a portion of the wall of a cylinder, said lens having an inner concave surface and an outer convex surface, and a thickness therebetween, wherein the radius ($R_1$) from the axis of said cylinder to an arc defining said inner concave surface is a substantially constant radius in the range of about $2\frac{1}{2}$ inches to about $4\frac{1}{2}$ inches; and means for mounting said lens on said lens-receiving portion of said frame.

2. The lens of claim 1, wherein the ratio of $d_2$ to L is in the range of about 0.30 to about 3.50.

3. The lens of claim 1, wherein $R_1$ is in the range of from about $3\frac{1}{2}$ inches to about 4 inches.

4. The lens of claim 1, wherein the ratio of $R_1$ to L is in the range of from about 0.35 to 0.80.

5. The lens of claim 1, wherein said arc length L comprises a central region which is substantially symmetrically located with respect to said nosepiece and a pair of distal regions adjacent either side of said central region, said thickness of said lens being in at least one point in said central region greater than the thickness of said lens at any point within at least one of said distal regions.

6. The lens of claim 5, wherein said central region is symmetrically located with respect to the midpoint along said arc length L, and wherein the thickness of said lens at said midpoint is between about 0.055 and about 0.070 inch.

7. The lens of claim 6, wherein the thickness of said lens at a point approximately 45° along said arc length from said midpoint is from about 40% to about 99% of the thickness of said lens at said midpoint.

8. The lens of claim 6, wherein the thickness of said lens at a point about 45° along said arc length of said lens from said midpoint is about 75% to about 98% of the thickness of said lens at said midpoint.

9. The lens of claim 5, wherein the thickness of said lens at said midpoint is between about 0.060 to about 0.070 inch, and the thickness of said lens in each of said distal regions is between about 0.040 and about 0.050 inch.

10. An arcuately molded lens for eyeglasses for participation in active sports, such as biking, skiing, and the like, said lens comprising:

a single pane, unitary lens having a top edge and a bottom edge, said bottom edge having a nosepiece opening formed therein for mounting said lens on the nose of the wearer, said lens having a bridge portion over said nosepiece opening, the distance separating the lower edge of the bridge portion and the top edge of the lens being defined as $d_1$ and the distance separating the top edge of the lens and the bottom edge of the lens being defined as $d_2$, wherein $d_1$ is in the range of about $\frac{3}{4}$ inch to $1\frac{1}{2}$ inches, and $d_2$ is in the range of about $1\frac{3}{4}$ inches to $2\frac{3}{4}$ inches, said dimensions providing optimum interception of light rays while allowing sufficient ventilation around the face of the wearer while participating in active sports, said lens having in its as-molded condition an arcuate cross-sectional configuration wherein the arc length (L) of said lens is in the range of from about $5\frac{1}{2}$ inches to 7 inches, and wherein the plane of said lens lies substantially in a cylinder, said lens having an inner concave surface and an outer convex surface and a thickness therebetween, wherein the radius ($R_1$) from the axis of said cylinder to an arc defining said inner concave surface is a substantially constant radius in the range of about 2.5 inches to about 4.5 inches, and wherein the ratio of $d_2$ to L is in the range of from about 0.30 to about 3.50.

11. The lens of claim 10, wherein the ratio of $d_1$ to L is in the range of from about 0.20 to about 0.035.

12. The lens of claim 10, wherein the ratio of $d_2$ to $R_1$ is in the range of from about 1.0 to about 0.44.

13. An arcuately molded lens for eyeglasses, said lens being suitable for participation in active sports, such as biking, skiing, and the like, said lens comprising:
    a single pane, unitary lens having an upper edge and a lower edge, said lower edge having a nosepiece opening formed therein for mounting said lens on the nose of the wearer,
    the distance separating the upper edge and the lower edge of the lens being in the range of from about $1\frac{3}{4}$ inches to about $2\frac{3}{4}$ inches,
    said lens having an arcuate cross-section configuration in its as-molded condition which substantially defines the wall of a cylinder,
    said lens having an inner concave surface and an outer convex surface and a thickness therebetween, wherein the radius ($R_1$) from the axis of said cylinder to an arc defining said inner concave surface is a substantially constant radius in the range of about $2\frac{1}{2}$ inches to about $4\frac{1}{4}$ inches.

14. An arcuately molded lens for eyeglasses, said lens being suitable for participation in active sports, such as biking, skiing, and the like, said lens comprising:
    a single pane, unitary lens having an upper edge and a lower edge, said lower edge having a nosepiece opening formed therein for mounting said lens on the nose of the wearer,
    said lens having an arcuate cross-sectional configuration in its as-molded condition which substantially defines the wall of a cylinder,
    said lens having an inner concave surface and an outer convex surface and a thickness therebetween, wherein the radius ($R_1$) from the axis of said cylinder to an arc defining said inner concave surface is a substantially constant radius in the range of about $2\frac{1}{2}$ inches to about $4\frac{1}{4}$ inches.

15. The lens of claim 14, wherein said arcuate crossectional configuration of said lens is comprised of a central region and a pair of adjacent, distal regions, the thickness of said lens in said distal regions being less than the average thickness of said lens in said central region.

16. The lens of claim 15, wherein the thickness of said lens at the midpoint of said central region tapers gradually to a reduced thickness in said distal regions.

* * * * *

UNITED STATES PATENT AND TRADEMARK OFFICE
CERTIFICATE OF CORRECTION

PATENT NO. : 4,859,048
DATED : August 22, 1989
INVENTOR(S) : James J. Jannard

It is certified that error appears in the above-identified patent and that said Letters Patent is hereby corrected as shown below:

In Column 3, at line 18, change "description of the" to --brief description of the--.

In Column 5, at line 59, change "wear's" to --wearer's--.

In Column 9, at line 46, change "bright" to --bridge--.

In Column 9, at line 52, change "1/2" to --1 1/2--.

In Column 12, at line 17, change "crosssectional" to --cross-sectional--.

In Column 9, at line 65, change "$R_1$" to --$R_2$--.

In Column 9, at line 60, change "plane" to --pane--.

In Column 10, at line 5, change "$R_1$" to --$R_2$--.

In Column 10, at line 7, change "$R_1$" to --$R_2$--.

In Column 10, at line 57, change "plane" to --pane--.

UNITED STATES PATENT AND TRADEMARK OFFICE
CERTIFICATE OF CORRECTION

PATENT NO.  : 4,859,048

DATED       : August 22, 1989

INVENTOR(S) : James J. Jannard

It is certified that error appears in the above-identified patent and that said Letters Patent is hereby corrected as shown below:

In Column 10, at line 61, change "$R_1$" to --$R_2$--.

In Column 11, at line 1, change "$R_1$" to --$R_2$--.

In Column 11, at line 22, change "$R_1$" to --$R_2$--.

In Column 12, at line 13, change "$R_1$" to --$R_2$--.

Signed and Sealed this

Thirteenth Day of August, 1991

*Attest:*

HARRY F. MANBECK, JR.

*Attesting Officer*     *Commissioner of Patents and Trademarks*